(12) United States Patent
    Prior

(10) Patent No.: US 10,639,044 B2
(45) Date of Patent: May 5, 2020

(54) LIGATION CLIP MODULE AND CLIP APPLIER

(71) Applicant: Covidien LP, Mansfield, MA (US)

(72) Inventor: Scott J. Prior, Shelton, CT (US)

(73) Assignee: COVIDIEN LP, Mansfield, MA (US)

( * ) Notice: Subject to any disclaimer, the term of this patent is extended or adjusted under 35 U.S.C. 154(b) by 241 days.

(21) Appl. No.: 15/703,193

(22) Filed: Sep. 13, 2017

(65) Prior Publication Data

US 2018/0116671 A1    May 3, 2018

Related U.S. Application Data

(60) Provisional application No. 62/414,820, filed on Oct. 31, 2016.

(51) Int. Cl.
| | | |
|---|---|---|
| *A61B 17/10* | (2006.01) | |
| *A61B 17/122* | (2006.01) | |
| *A61B 17/128* | (2006.01) | |
| *A61B 17/00* | (2006.01) | |

(52) U.S. Cl.
CPC ...... *A61B 17/1222* (2013.01); *A61B 17/1285* (2013.01); *A61B 2017/00473* (2013.01)

(58) Field of Classification Search
CPC ....... A61B 17/10; A61B 17/12; A61B 17/122; A61B 17/1222; A61B 17/128; A61B 17/1285; A61B 2017/0488
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |

(Continued)

FOREIGN PATENT DOCUMENTS

| | | |
|---|---|---|
| AU | 2013254887 A1 | 11/2013 |
| CA | 1163889 A | 3/1984 |

(Continued)

OTHER PUBLICATIONS

European Office Action corresponding to EP 12 152 989.5 dated May 4, 2015.

(Continued)

*Primary Examiner* — Melanie R Tyson

(57) ABSTRACT

A ligation clip module including a module housing that is compressible from an uncompressed condition to a compressed condition. The module housing includes a proximal portion, a distal portion, and a lumen extending therethrough. The ligation clip module further includes a pusher slidably disposed in the lumen of the module housing and a ligation clip disposed in the proximal portion of the module housing at a location distal of the pusher.

20 Claims, 9 Drawing Sheets

(56) References Cited

U.S. PATENT DOCUMENTS

| | | |
|---|---|---|
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A * | 10/1994 | Allen ............... A61B 17/122 |
| | | 227/901 |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A * | 3/1995 | Green ............... A61B 17/122 |
| | | 227/19 |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |

(56) References Cited

U.S. PATENT DOCUMENTS

| | | |
|---|---|---|
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A * | 8/1996 | Yoon ............... A61B 17/0057 227/901 |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A * | 10/1999 | Rousseau ............ A61B 17/1285 606/139 |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |

(56) References Cited

U.S. PATENT DOCUMENTS

| | | |
|---|---|---|
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |

(56) References Cited

U.S. PATENT DOCUMENTS

| | | |
|---|---|---|
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,887,553 B2 | 2/2011 | Lehman et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,885 B2 | 5/2011 | Sixto, Jr. et al. |
| 7,942,890 B2 | 5/2011 | D'Agostino et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,920,438 B2 | 12/2014 | Aranyi et al. |
| 8,939,974 B2 | 1/2015 | Boudreaux et al. |
| 8,945,151 B2 | 2/2015 | Salas |

(56) References Cited

U.S. PATENT DOCUMENTS

| | | |
|---|---|---|
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,282,972 B1 | 3/2016 | Patel et al. |
| 9,326,776 B2 | 5/2016 | Gadberry et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,445,810 B2 | 9/2016 | Cappola |
| 9,445,820 B2 | 9/2016 | Whiting |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,517,064 B2 | 12/2016 | Sarradon |
| 9,526,501 B2 | 12/2016 | Malkowski |
| 9,526,565 B2 | 12/2016 | Strobl |
| 9,545,254 B2 | 1/2017 | Sorrentino et al. |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,687,247 B2 | 6/2017 | Aranyi et al. |
| 9,717,504 B2 | 8/2017 | Huitema |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,782,181 B2 | 10/2017 | Vitali et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |

(56) References Cited

U.S. PATENT DOCUMENTS

| | | |
|---|---|---|
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0045816 A1 | 2/2015 | Aranyi et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2015/0351771 A1 | 12/2015 | Malkowski et al. |
| 2015/0351772 A1 | 12/2015 | Malkowski et al. |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0262764 A1 | 9/2016 | Gokharu |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 103251441 A | 8/2013 |
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0 406 724 A1 | 1/1991 |
| EP | 0514139 A2 | 11/1992 |
| EP | 0 732 078 A2 | 9/1996 |

(56) References Cited

FOREIGN PATENT DOCUMENTS

| | | |
|---|---|---|
| EP | 1769757 A1 | 4/2007 |
| EP | 3132756 A1 | 2/2017 |
| GB | 2073022 A | 10/1981 |
| JP | 2003-033361 A | 2/2003 |
| JP | 2006-154230 A | 6/2006 |
| JP | 2006-277221 A | 10/2006 |
| JP | 2008-017876 A | 1/2008 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 2001-66001 A2 | 9/2001 |
| WO | 2001-67965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

Australian Office Action corresponding to AU 2009212759 dated May 7, 2015.
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
Extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
International Search Report corresponding to International Application No. PCT-US08-59859, completed Sep. 14, 2008; dated Sep. 18, 2008; (2 Pages).
Extended European Search Report corresponding to European Application No. EP 07 25 3807.7, completed Nov. 7, 2008; dated Nov. 26, 2008; (11 Pages).
Extended European Search Report corresponding to European Application No. EP 09 25 2049.3, completed Dec. 11, 2009; dated Jan. 12, 2010; (3 Pages).
Extended European Search Report corresponding to European Application No. EP 09 25 2050.1, completed Dec. 23, 2009; dated Jan. 21, 2010; (3 Pages).
Extended European Search Report corresponding to European Application No. EP 09 25 2051.9, completed Dec. 21, 2009; dated Jan. 28, 2010; (3 Pages).
Extended European Search Report corresponding to European Application No. EP 09 25 2052.7, completed Nov. 16, 2009; dated Nov. 24, 2009; (3 Pages).

(56) References Cited

OTHER PUBLICATIONS

Extended European Search Report corresponding to European Application No. EP 09 25 2053.5, completed Nov. 24, 2009; dated Dec. 1, 2009; (3 Pages).
Extended European Search Report corresponding to European Application No. EP 09 25 2054.3, completed Jan. 7, 2010; dated Jan. 22, 2010; (3 Pages).
Extended European Search Report corresponding to European Application No. EP 09 25 2056.8, completed Jan. 8, 2010; dated Feb. 5, 2010; (3 Pages).
Extended European Search Report corresponding to European Application No. EP 10 25 0497.4, completed May 4, 2010; dated May 12, 2010; (6 Pages).
Extended European Search Report corresponding to European Application No. EP 10 25 2079.8, completed Mar. 8, 2011; dated Mar. 17, 2011; (3 Pages).
European Search Report corresponding to European Application No. EP 05 81 0218.7, completed Apr. 18, 2011; dated May 20, 2011; (3 pages).
European Search Report corresponding to European Application No. EP 05 80 7612.6, completed May 2, 2011; dated May 20, 2011; (3 pages).
Extended European Search Report corresponding to European Application No. EP 10 25 1737.2, completed May 9, 2011; dated May 20, 2011; (4 pages).
Extended European Search Report corresponding to European Application No. EP 11 25 0214.1, completed May 25, 2011; dated Jun. 1, 2011; (3 Pages).
Extended European Search Report corresponding to European Application No. EP 11 00 2681.2, completed May 31, 2011; dated Jun. 10, 2011; (3 Pages).
European Search Report corresponding to European Application No. EP 05 80 2686.5, completed Jan. 9, 2012; dated Jan. 18, 2012; (3 Pages).
Extended European Search Report corresponding to European Application No. EP 12 15 1313.9, completed Mar. 20, 2012 and dated Apr. 12, 2012; (5 Pages).
Extended European Search Report corresponding to European Application No. EP 12 16 1291.5, completed Apr. 24, 2012 and dated May 4, 2012; (5 Pages).
Extended European Search Report corresponding to European Application No. EP 12 16 5891.8, completed Jun. 12, 2012 and dated Jun. 20, 2012; (6 Pages).
Extended European Search Report corresponding to European Application No. EP 12 16 2288.0, completed Jun. 4, 2012 and dated Jul. 7, 2012; (6 Pages).
Extended European Search Report corresponding to European Application No. EP 12 16 4955.2, completed Aug. 23, 2012 and dated Sep. 4, 2012; (5 Pages).
Extended European Search Report corresponding to European Application No. EP 11 25 0754.6, completed Oct. 22, 2012 and dated Oct. 31, 2012; (6 Pages).
Extended European Search Report corresponding to European Application No. EP 12 18 6401.1, completed Nov. 22, 2012 and dated Nov. 30, 2012; (7 Pages).
Extended European Search Report corresponding to European Application No. EP 12 18 6448.2, completed Nov. 28, 2012 and dated Dec. 10, 2012; (6 Pages).
Extended European Search Report corresponding to European Application No. EP 12 19 1706.6, completed Dec. 19, 2012 and dated Jan. 8, 2013; (6 Pages).
Extended European Search Report corresponding to EP 12 19 8745.7, completed Mar. 19, 2013 and dated Apr. 11, 2013; (8 Pages).
Extended European Search Report corresponding to EP 12 15 2989.5, completed Apr. 9, 2013 and dated Apr. 18, 2013; (9 Pages).
Extended European Search Report corresponding to EP 08 73 2820.9, completed Jul. 2, 2013 and dated Jul. 9, 2013; (10 Pages).
Extended European Search Report corresponding to EP 13 17 2008.8, completed Aug. 14, 2013 and dated Aug. 28, 2013; (8 Pages).
Extended European Search Report corresponding to EP 13 16 6382.5, completed Nov. 19, 2013 and dated Nov. 28, 2013; (8 Pages).
Extended European Search Report corresponding to EP 11 25 0194.5, completed Nov. 25, 2013 and dated Dec. 3, 2013; (8 Pages).
Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 10 25 2112.7, completed Jul. 29, 2014 and dated Aug. 5, 2014; (8 pp).
Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extnded European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.

(56) References Cited

OTHER PUBLICATIONS

Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.

\* cited by examiner

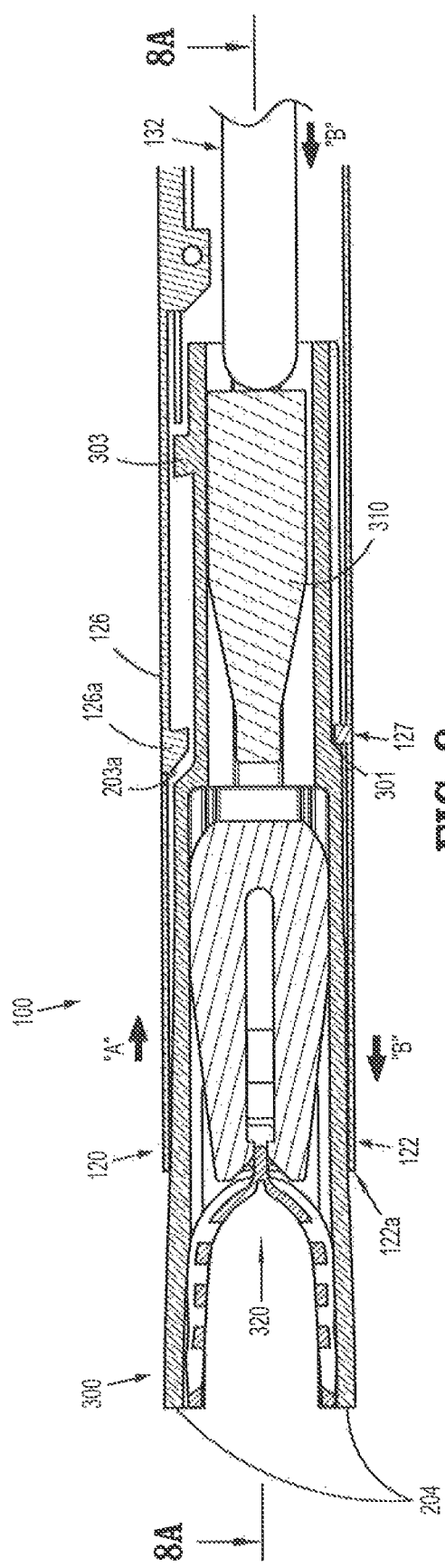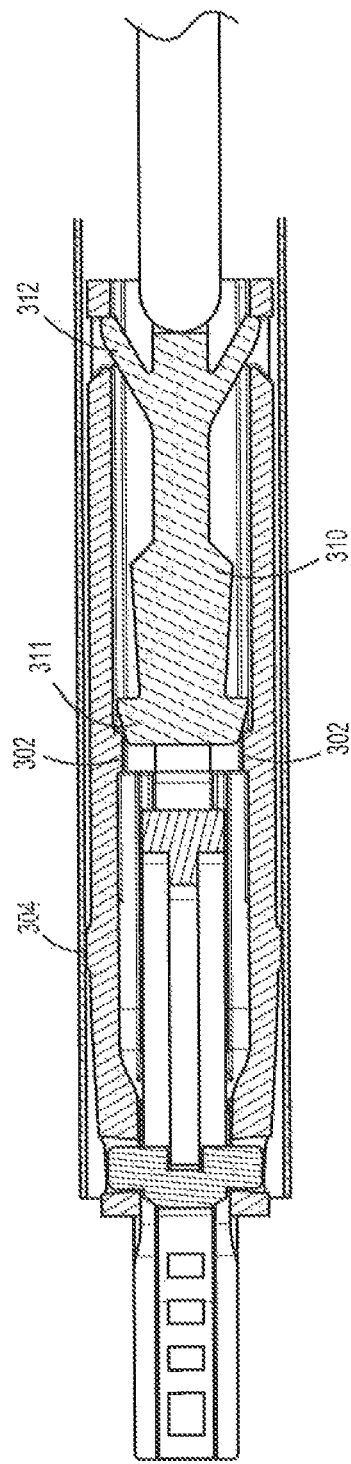

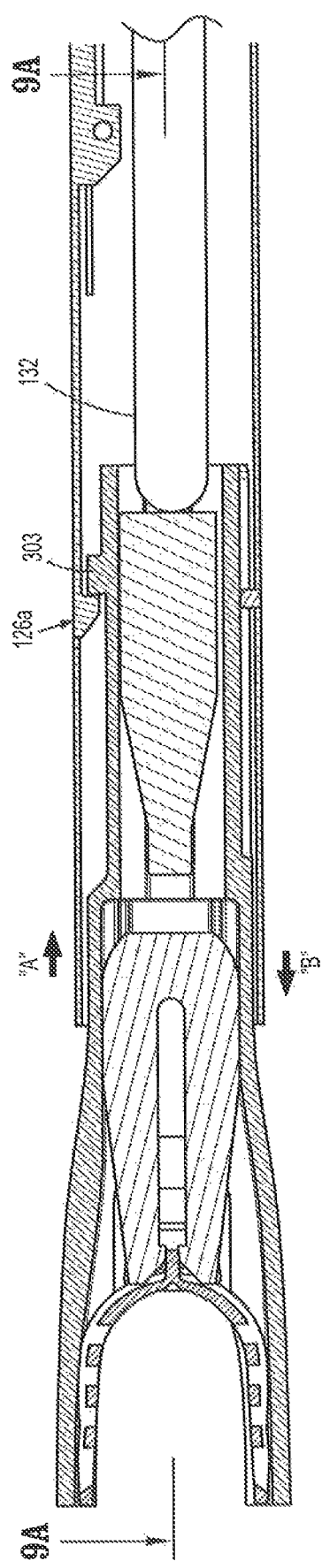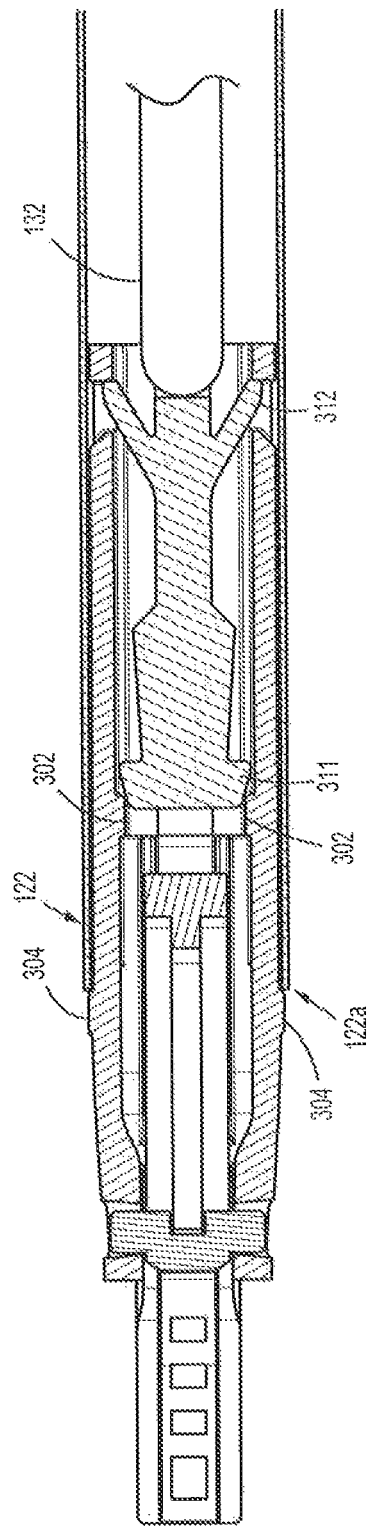

LIGATION CLIP MODULE AND CLIP APPLIER

CROSS-REFERENCE TO RELATED APPLICATIONS

This application claims the benefit of and priority to U.S. Provisional Patent Application No. 62/414,820 filed Oct. 31, 2016, the entire disclosure of which is incorporated by reference herein.

BACKGROUND

1. Technical Field

The present disclosure generally relates to a medical instrument for use with a surgical ligation clip applier. More particularly, the present disclosure is directed to a single-fire module for housing a two-part ligation clip for securing and closing the two-part ligation clip around a vessel to be occluded.

2. Background of Related Art

Surgical procedures often require ligation (e.g., the closing off) of blood vessels to control or stop bleeding. In a laparoscopic surgical procedure, a small entrance incision is made in the skin through which a surgeon may introduce a hollow tube or access port (e.g., trocar). The access port allows the surgeon to insert a number of different surgical instruments therethrough for performing surgical procedures far removed from the incision.

During laparoscopic procedures, the termination of the flow of blood or another fluid through one or more vessels is often required. The surgeon may apply a surgical clip to the blood vessel or other duct to prevent the flow of bodily fluids therethrough. Typically, a module containing the clip is attached to the distal end of a ligation clip applier. The ligation clip applier uses a plunger or piston to fire the clip onto the vessel. Once applied to the vessel, the compressed clip terminates the flow of fluid therethrough.

Ligation clips are typically fabricated from a biocompatible material, such as metal alloys or polymers. For certain procedures, it may be advantageous to use bioabsorbable clips (e.g., instead of metal alloy or polymer clips) because they can be absorbed into the body over time, rather than remaining in the body indefinitely. Due to their unique properties, it is difficult to scale bioabsorbable ligation clips down in size while still maintaining their functionality (e.g., strength, degradation properties, and the like). In contrast, metal alloy or polymeric clips may be scaled down in size without suffering drawbacks, which allows them to fit in smaller module housings. Since a larger module housing is required for bioabsorbable clips, a larger clip applier shaft, entrance incision, and access port are also required.

Accordingly, a need exists for a module housing that can accommodate larger bioabsorbable clips and that can be used with clip appliers and access ports designed for smaller module housings and/or ligation clips.

SUMMARY

The present disclosure relates to ligation clip modules for use with endoscopic surgical clip appliers.

According to an aspect of the present disclosure, a ligation clip module is provided and includes a module housing that is compressible from an uncompressed condition to a compressed condition. The module housing includes a proximal portion and a distal portion, and a lumen extending therethrough. The ligation clip module further includes a pusher slidably disposed in the lumen of the module housing, and a ligation clip disposed in the proximal portion of the module housing at a location distal of the pusher.

The module housing may include an outer surface having a first protrusion extending therefrom and an immobilizer extending into the lumen thereof.

The pusher may include a pusher body having an enlarged proximal portion and an enlarged distal portion.

The module housing may be compressed from the uncompressed condition to the compressed condition such that the first protrusion of the module housing is advanceable into an open end of a distal end of a shaft of a ligation clip applier, and such that the proximal end of the module housing is selectively connected to the distal end of the shaft of the ligation clip applier. The module housing may thus be maintained in the compressed condition.

In use, when the module housing is in the compressed condition, the immobilizer of the module housing may be disposed between the enlarged proximal portion and the enlarged distal portion of the pusher body such that the pusher is prevented from axial movement within the module housing.

In use, when the module housing is in the compressed condition and disposed in the distal end of the ligation clip applier, the enlarged proximal portion of the pusher may be engagable by an advancing mechanism of the ligation clip applier such that the enlarged proximal portion of the pusher engages the immobilizer of the module housing whereby the module is urged axially toward the distal end of the shaft of the ligation clip applier.

Also in use, when the first protrusion of the module housing is urged distally past the distal end of the shaft of the ligation clip applier, the module housing may be free to return to the uncompressed condition from the compressed condition.

The ligation clip may be a two-part ligation clip having a first part formed to be closed about a vessel and a second part moveable relative to the first part to cause the first part to close.

The ligation clip may be formed from a bioabsorbable material.

The pusher may include retaining wings disposed on the pusher body for retaining the pusher in the module housing.

The module housing may include a recess formed in the outer surface thereof for receiving a latch of the ligation clip applier, whereby the module housing may be selectively fixedly secured to the distal end of the shaft of the ligation clip applier.

According to another aspect of the present disclosure, a ligation clip module is provided for selective connection to a handle assembly of a ligation clip applier and actuatable by an advancing mechanism of the handle assembly. The ligation clip module includes a module housing that is compressible from an uncompressed condition to a compressed condition. The module housing includes an outer surface having a first protrusion extending therefrom, a proximal end being configured for selective connection to a distal end of a shaft of the ligation clip applier, a distal end, and a lumen extending therethrough and having an immobilizer extending thereinto.

The ligation clip module further includes a pusher slidably disposed in the lumen of the module housing. The pusher includes a pusher body having an enlarged proximal portion and an enlarged distal portion.

The ligation clip module also includes a ligation clip slidably disposed in the lumen of the module housing at a location distal of the pusher.

In use, the module housing is compressed from the uncompressed condition to the compressed condition such that the first protrusion of the module housing is advanceable into an open end of the distal end of the shaft of the ligation clip applier, and such that the proximal end of the module housing is selectively connected to the distal end of the shaft of the ligation clip applier, and wherein the module housing is maintained in the compressed condition.

Also in use, when the module housing is in the compressed condition, the immobilizer of the module housing is disposed between the enlarged proximal portion and the enlarged distal portion of the pusher body such that the pusher is prevented from axial movement within the module housing.

According to yet another aspect of the present disclosure, a ligation clip applier is provided and includes a handle assembly and a ligation clip module that is selectively connectable to the shaft of the handle assembly. The handle assembly includes a fixed handle, a trigger, a shaft extending from the fixed handle, and an advancing mechanism supported in the fixed handle and the shaft, the advancing mechanism being actuatable by the trigger.

The ligation clip module includes a module housing that is compressible from an uncompressed condition to a compressed condition. The module housing includes a proximal portion and a distal portion, and a lumen extending therethrough. The ligation clip module further includes a pusher slidably disposed in the lumen of the module housing, and a ligation clip disposed in the proximal portion of the module housing at a location distal of the pusher.

BRIEF DESCRIPTION OF THE DRAWINGS

Objects and features of the present disclosure will become apparent to those of ordinary skill in the art when descriptions of various embodiments thereof are read with reference to the accompanying drawings, of which:

FIG. 8 is an enlarged cross-sectional, side elevational view of a distal end of a neck portion of the ligation clip applier of FIG. 1, with a loaded ligation clip module, according to another embodiment of the present disclosure, attached thereto in a compressed condition;

FIG. 8A illustrates another cross-sectional view of FIG. 8;

FIG. 9 is an enlarged cross-sectional, side elevational view of the distal end of the neck portion of the ligation clip applier of the neck portion of the ligation clip applier of FIG. 8, with a loaded clip module attached thereto in an extended condition; and FIG. 9A illustrates another cross-sectional view of FIG. 9.

DETAILED DESCRIPTION OF THE EMBODIMENTS

Figure 1:
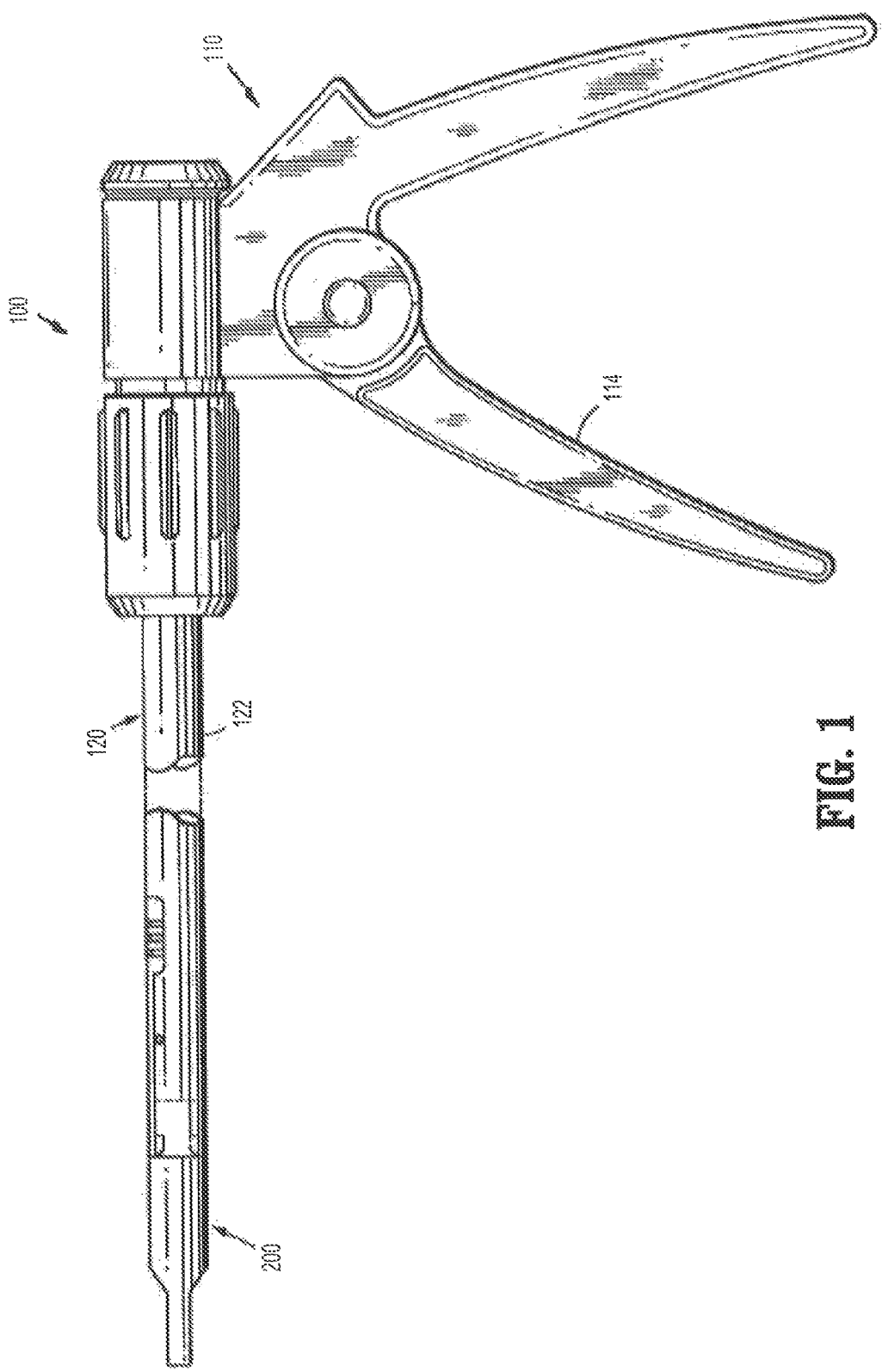
FIG. 1 is a side elevational view of a ligation clip applier in accordance with the present disclosure.

Embodiments of ligation clips, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the instrument which is closer to the user and the term "distal" refers to the end of the instrument which is further away from the user.

Figure 2:
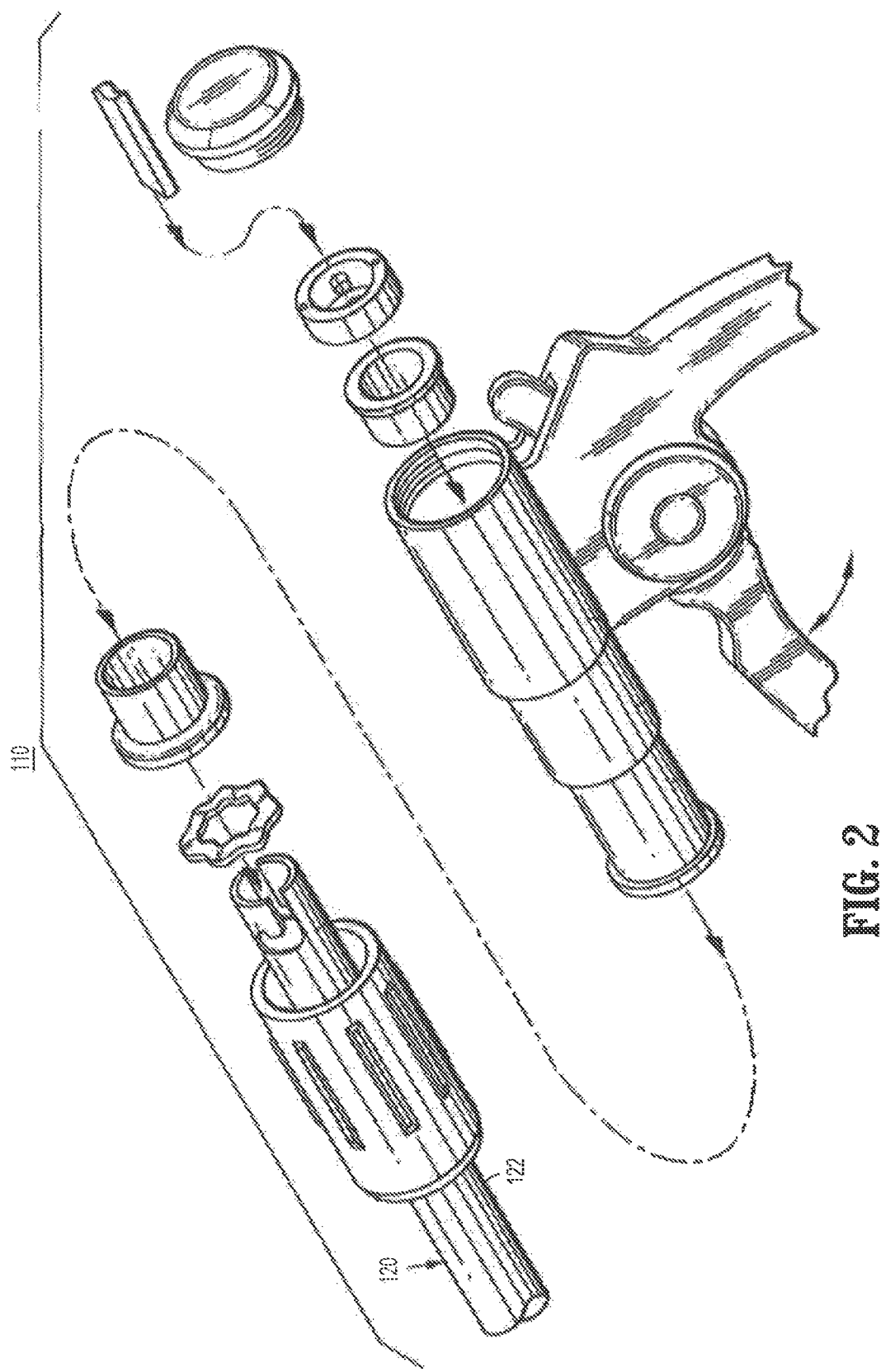
FIG. 2 is a perspective view, with parts separated, of a handle assembly and a proximal end of a neck portion of the ligation clip applier of FIG. 1.

As shown in FIGS. 1 and 2, a ligation clip applier, in accordance with an embodiment of the present disclosure, is generally designated as 100. Ligation clip applier 100 includes a handle assembly 110, an elongated and round or cylindrical neck portion or assembly 120 projecting from or extending from handle assembly 110, and a ligation clip module 200 (FIG. 5) that can be removably and selectively mounted on a distal end of neck portion 120. As will be described in greater detail below, in operation, as handle assembly 110 is actuated, a single ligation clip 220 (FIG. 5) is fired and formed around a vessel to be ligated.

Figure 3:
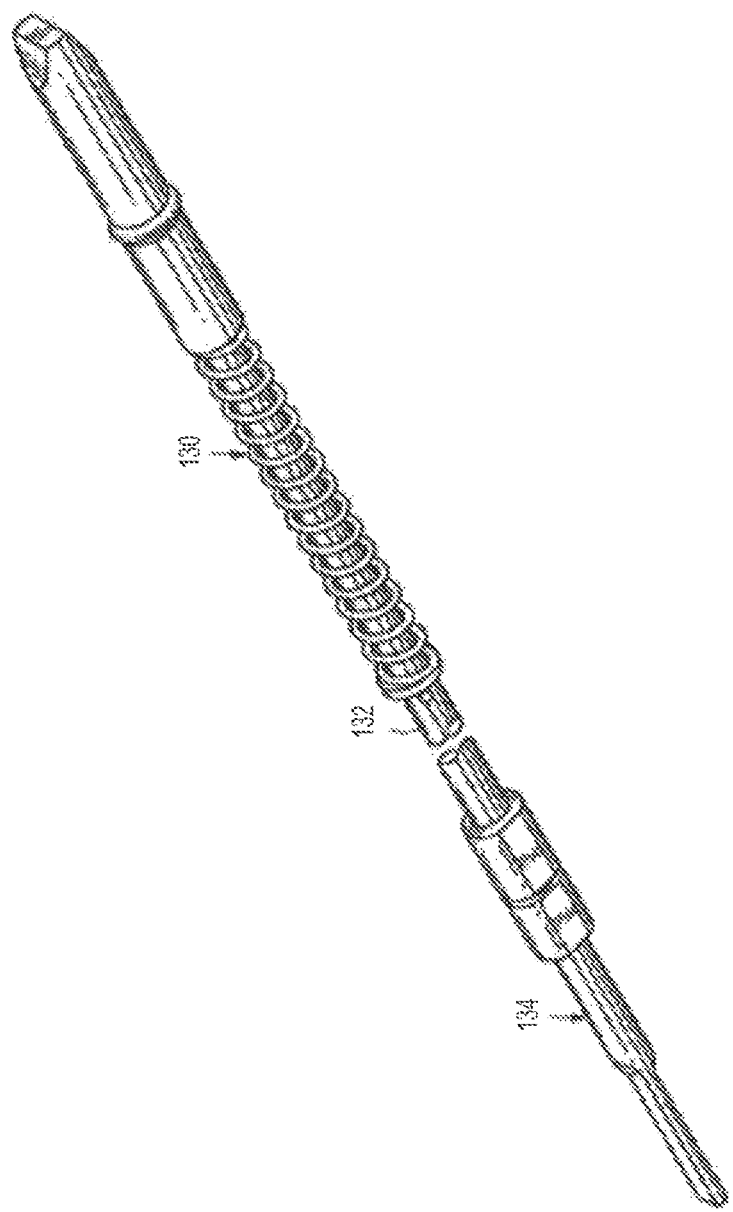
FIG. 3 is a perspective view of an advancing mechanism of the ligation clip applier of FIG. 1.
Figure 4:
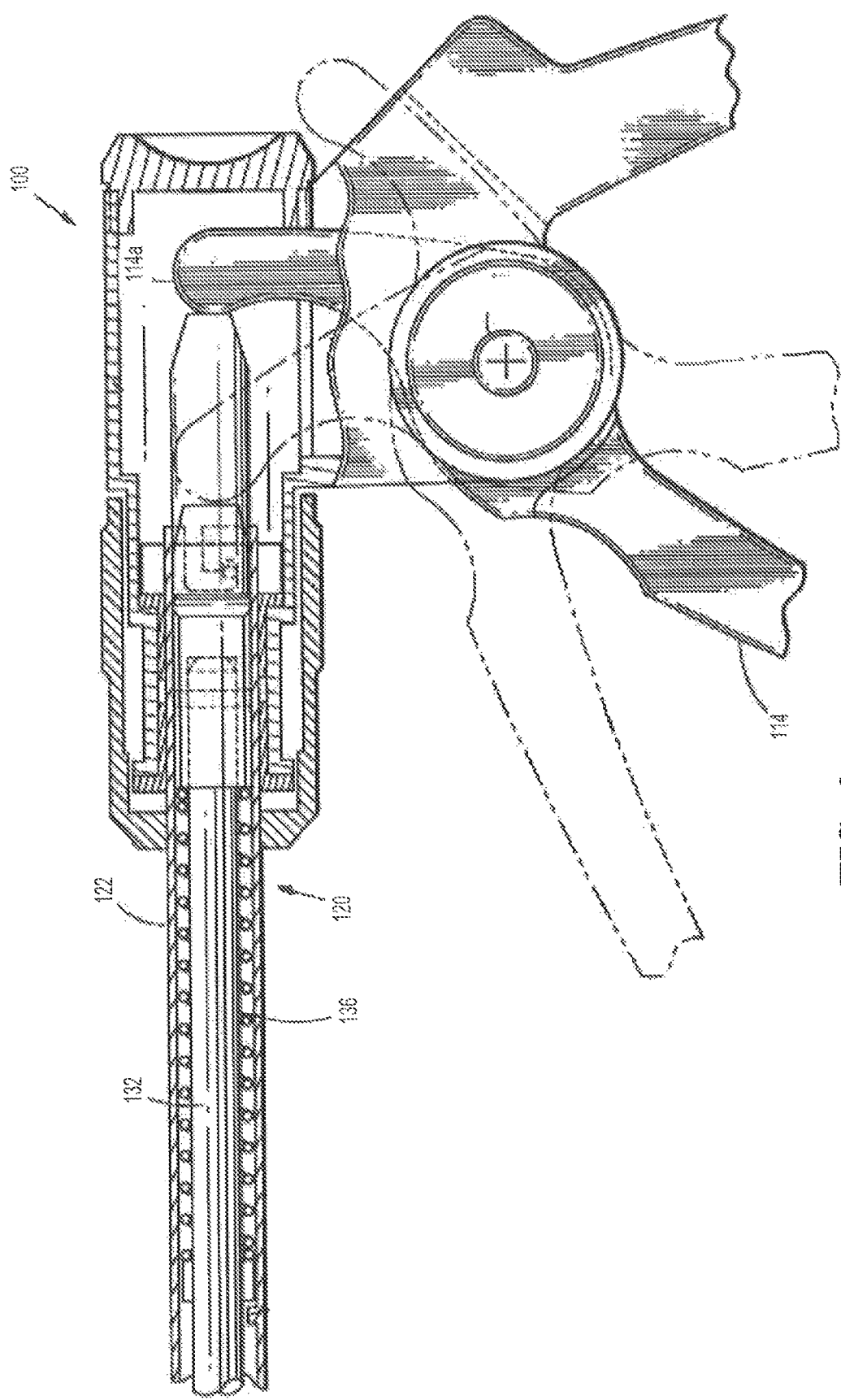
FIG. 4 is a cross-sectional, elevational view of the proximal end of the ligation clip applier illustrating the handle assembly in three different positions.

With reference to FIGS. 3 and 4, neck portion 120 includes an advancing mechanism 130 slidably disposed within hollow shaft 122 thereof. Advancing mechanism 130 includes an advancing shaft 132 that supports an actuator 134 at its distal end portion.

With reference to FIG. 4, when squeezable trigger 114 of handle assembly 110 is pivoted in the counterclockwise direction, a top or actuating end 114a of squeezable trigger 114 engages a proximal end of the advancing shaft 132 thereby urging advancing shaft 132 distally against the biasing force of spring 136.

For a more detailed discussion of the construction and operation of ligation clip applier 100, and specifically handle assembly 110 thereof, reference may be made to U.S. Pat. No. 5,354,304, the entire content of which is incorporated herein by reference.

Figure 5:
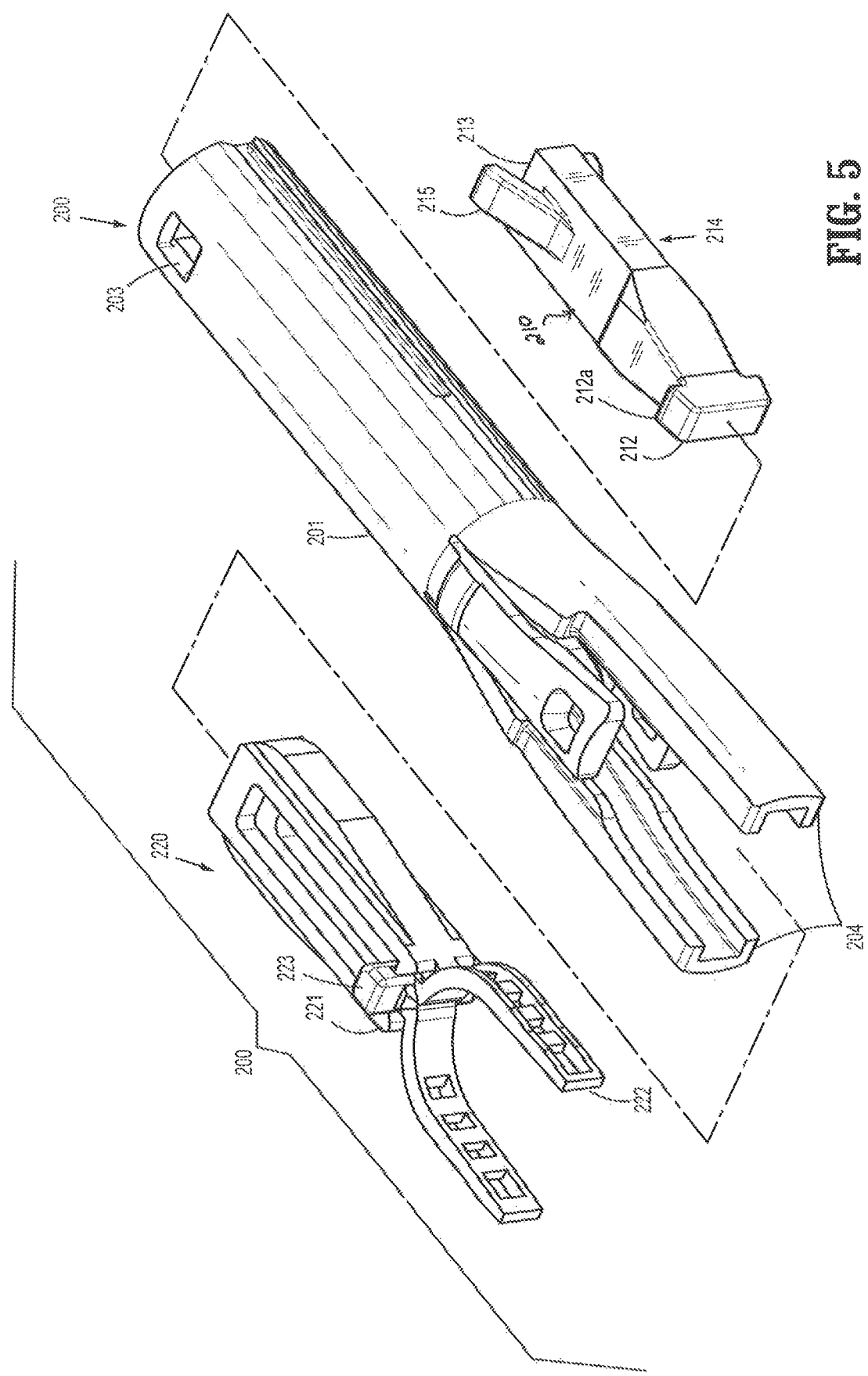
FIG. 5 is an exploded perspective view of a ligation clip module.
Figure 6:
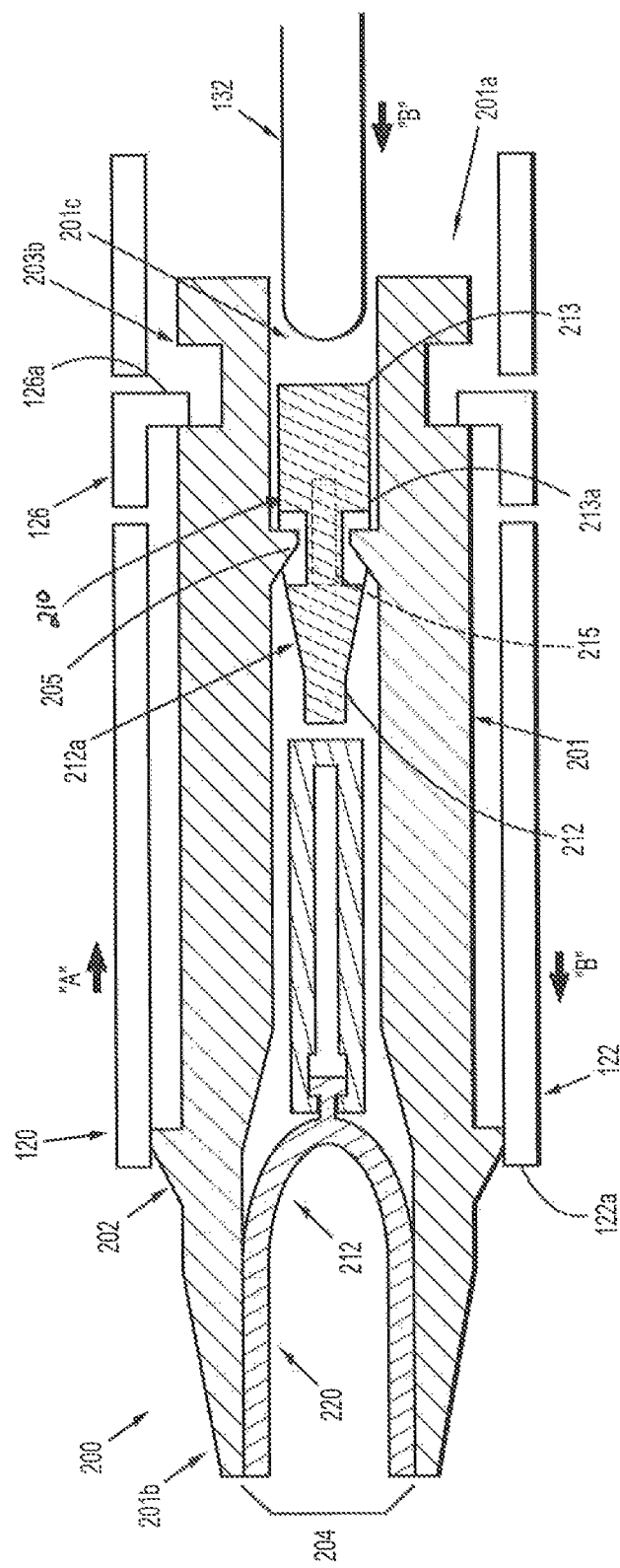
FIG. 6 is an enlarged cross-sectional, side elevational view of a distal end of a neck portion of the ligation clip applier of FIG. 1, with a loaded ligation clip module attached thereto in a compressed condition.

Referring now to FIGS. 5 and 6, ligation clip module 200 is shown in accordance with an exemplary embodiment of the present disclosure. Ligation clip module 200 includes a module housing 201, a protrusion 202 extending from an outer surface of module housing 201, a groove 203 formed in the outer surface of module housing 201, and jaws 204 extending distally from module housing 201. Module housing 201 of ligation clip module 200 includes a proximal end portion 201a, a distal end portion 201b and a lumen 201c extending therethrough. Protrusion 202 of ligation clip module 200 may be any type of protuberance or plurality of protuberances, such as posts, flanges, fins, bumps, lumps, knobs, ridges, or the like. In an embodiment, protrusion 202 may be disposed radially on the outer surface of module housing 201. Groove 203 of module housing 201 may be any type of surface for receiving a pawl 126a of a latch 126, such as an indentation, notch, slot, recess, or the like (see FIG. 6).

Ligation clip module 200 includes a pusher 210 disposed within lumen 201c (FIGS. 5-7) of module housing 201.

Pusher 210 may include a distal end 212 having an enlarged distal portion 212a, a proximal end 213, and a pusher body 214. Pusher 210 may have retaining wings, flanges or tabs 215 (FIGS. 5-7) extending from pusher body 214, for retaining pusher 210 in module housing 201. For a detailed description of the construction and operation of wings 215 of pusher 210 of ligation clip module 200, reference may be made to U.S. Pat. No. 5,972,003, the entirety of which is incorporated herein by reference.

Ligation clip module 200 includes a ligation clip 220 disposed in lumen 201c of module housing 201 that is releasably supported adjacent the distal end 201b of module housing 201. Ligation clip 220 includes a U-shaped clip body 221 slidably connected to a Y-shaped clip track 222 through a post 223 located at an apex of clip track 222. To close ligation clip 220 around a vessel, clip track 222 is held stationary by post 223 as clip body 221 is moved distally toward clip track 222. This movement urges the legs of clip body 221 outwardly as they begin to close over and clamp around the arms of clip track 222. For a detailed description of the construction and operation of ligation clip 220, reference may be made to U.S. Pat. Nos. 4,590,937, 5,306, 283, and 5,972,003, the entirety of each of which is incorporated herein by reference.

FIG. 6 illustrates how ligation clip module 200 is compressed, inserted, and connected to the neck portion 120 of hollow shaft 122 according to an exemplary embodiment of the present disclosure. In accordance with the present disclosure, ligation clip module 200 is compressible such that relatively larger ligation clips 220 may be inserted into hollow shafts 122 of clip appliers 100 that are designed for relatively smaller ligation clips, e.g., a ligation clip 220 designed for a 10 mm shaft clip applier and/or access port may be inserted into a 5 mm shaft clip applier and/or access port. As such, a surgeon may make an entrance incision of a relatively reduced size for an access port during laparoscopy (which is ultimately less invasive to the patient), while still possessing the versatility and/or maintaining the functionality of a relatively larger ligation clip. Ligation clip module 200 may be particularly useful with bioabsorbable clips, which, due to their material properties, may be difficult to scale down in size without reducing their effectiveness.

With continued reference to FIG. 6, to begin insertion of ligation clip module 200 into the open distal end of hollow shaft 122 of ligation clip applier 100, a surgeon may manually compress jaws 204 together such that ligation clip module 200 is moved from an uncompressed position to a compressed position, so that the overall diameter of ligation clip module 200 is reduced to a diameter smaller than an inner diameter of hollow shaft 122. In an embodiment, ligation clip module 200 may be formed from any compressible, resilient material such that ligation clip module 200 is movable from the uncompressed position to the compressed position. Compressing jaws 204 of ligation clip module 200 permits protrusion 202 to be inserted into hollow shaft 122 and into neck portion 120 of ligation clip applier 100. The inner walls of hollow shaft 122 serve to keep ligation clip module 200 in the compressed position by exerting a radial force onto ligation clip module 200 and protrusion 202.

In order to load and secure ligation clip module 200 in the neck portion 120 of hollow shaft 122 of ligation clip applier 100, a spring-loaded latch 126 is pivotably mounted in a wall of hollow shaft 122. Latch 126 has a pawl 126a extending therefrom. The surgeon will then advance ligation clip module 200 in the direction of arrow "A" (FIGS. 6 and 7) until pawl 126a of latch 126 catches within groove 203 of module housing 201 of ligation clip module 200 such that ligation clip module 200 is securely locked in neck portion 120. As will be described in greater detail below, groove 203 of module housing 201 is dimensioned such that ligation clip module 200 may move axially within hollow shaft 122 of ligation clip applier 100, and have its axial movement limited by pawl 126a of latch 126.

As so loaded, ligation clip module 200 remains in the compressed position. At least a portion of ligation clip module 200 may remain outside the open distal end of hollow shaft 122, such as, for example, the portion of ligation clip module 200 distal of protrusion 202. Alternatively (not shown), while in the compressed position, the entire ligation clip module 200 may be inserted within the neck portion 120 of hollow shaft 122 of ligation clip applier 100.

While ligation clip module 200 is inserted into neck portion 120 of hollow shaft 122 and in the compressed position (FIG. 6), an immobilizer 205 extending into lumen 201c of module housing 201 is disposed on pusher body 214 of pusher 210, such that axial movement of pusher 210 through module housing 201 is restricted. In this position, ligation clip module 200 together with clip applier 100 may be advanced down an access port and into a patient's body. In embodiments, immobilizer 205 of ligation clip module 200 may be any type of surface disposed on or extending inwardly from an inner surface of module housing 201, such as a protrusion or protuberance.

Figure 7:
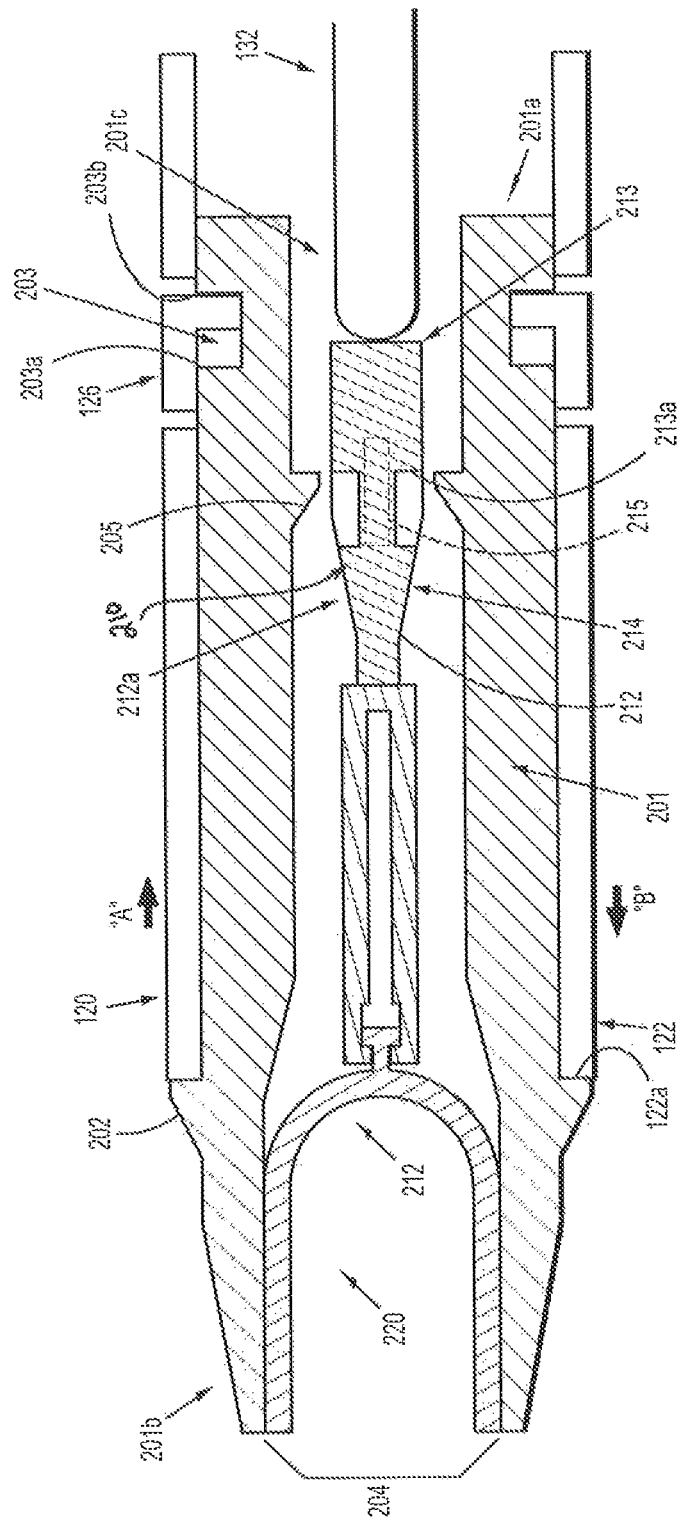
FIG. 7 is an enlarged cross-sectional, side elevational view of the distal end of the neck portion of the ligation clip applier of the neck portion of the ligation clip applier of FIG. 6, with a loaded clip module attached thereto in an extended condition.

In order to prepare ligation clip applier 100, together with loaded ligation clip module 200 for use and firing, a surgeon will partially squeeze or actuate trigger 114 of handle assembly 110 such that advancing shaft 132 abuts the proximal end 213 of pusher 210. Since immobilizer 205 of module housing 201 has restricted the movement of pusher 210, the entire ligation clip module 200 will be advanced distally forward in direction "B" of neck portion 120, as shown in FIG. 6. As ligation clip module 200 continues to be advanced distally, protrusion 202 will ultimately clear and snap over the open distal end of hollow shaft 122 such that jaws 204 are free to resiliently flex radially outward to the uncompressed position, as shown in FIG. 7. Distal advancement of ligation clip module 200 will stop when pawl 126a of latch 126 abuts against a shoulder 203b of groove 203. Accordingly, any further distal advancement of advancing shaft 132 will distally advance pusher 210 of ligation clip module 200 relative to module housing 201 of ligation clip module 200. Additionally, with protrusion 202 of ligation clip module 200 disposed distally of and/or in abutment with rim 122a of hollow shaft 122, ligation clip module 200 is prevented from proximal axial movement, in direction "A," into neck portion 120 of hollow shaft 122.

Additionally, pawl 126a of latch 126 enters into groove 203 of ligation clip module 200, whereby ligation clip module 200 is prevented from advancing forward in direction "B." In this position, and with reference to FIG. 7, ligation clip module 200 is uncompressed and fully secured within neck portion 120 of hollow shaft 122, and is ready for use in a firing configuration of clip applier 100. In an embodiment, a surgeon may be provided with auditory (i.e., a "snap" or "click") or tactile feedback to indicate that protrusion 202 has advanced past the open distal end of hollow shaft 122 and that pawl 126a of latch 126 is disposed within groove 203 of ligation clip module 200.

In this firing configuration, jaws 204 of ligation clip module 200 may be used to manipulate tissue when positioning ligation clip 220 about a vessel to be ligated. When ligation clip module 200 is in the uncompressed position, immobilizer 205 of module housing 201 has disengaged from pusher body 214, such that pusher 210 is no longer restrained by immobilizer 205. Once the desired vessel (not shown) has been located and inserted between jaws 204 of ligation clip module 200, the surgeon may then partially squeeze trigger 114 such that advancing shaft 132 of ligation clip applier 100 abuts proximal end 213 of pusher 210 of ligation clip module 200. In addition, distal end 212 of pusher 210 abuts with the proximal end of U-shaped clip body 221 of ligation clip 220, such that pusher 210 may be advanced distally to expel ligation clip 220 from ligation clip module 200, and clamp ligation clip 220 onto the vessel.

As trigger 114 is fully actuated, pusher 210 will advance U-shaped clip body 221 of ligation clip 220 distally over Y-shaped clip track 222 thereof, such that ligation clip 220 may be fully formed over the vessel. Following formation of ligation clip 220, trigger 114 is released, whereby return spring 136 is free to expand and thus withdraw advancing shaft 132 of neck portion 120. Ligation clip applier 100 along with ligation clip module 200 may be pulled back or withdrawn through the access port. The access port will cause jaws 204 and ligation module 220 to compress passively through the retracting motion. Pawl 126a of latch 126 will prevent ligation module 200 from prematurely or unintentionally detaching from hollow shaft 122 and neck portion 120.

Following removal of ligation clip applier 100 and ligation clip module 200 from a patient's body, latch 126 may be actuated to raise and disengage pawl 126a thereof from groove 203 of ligation clip module 200 to permit disconnection of spent ligation clip module 200 from hollow shaft 122 and neck portion 120.

A new ligation clip module 200 can then be inserted and secured in neck portion 120 of hollow shaft 122 (in the manner described above), and ligation clip applier 100 is once again ready to fire another ligation clip 220. Ligation clips 220 may be contained in kit form containing a plurality of clips, such as, for example, six (6) clips of the like. Kits may be loaded with a full set of metal clips (e.g., titanium, stainless steel or metal alloys), a full set of polymer clips (e.g., biocompatible or bioabsorbable), or a combination thereof.

In an alternative embodiment, as shown in FIGS. 8, 8A, 9 and 9A, a ligation clip module 300 may be loaded into neck portion 120 of hollow shaft 122 of ligation clip applier 100 while in a rest or uncompressed position. During loading of ligation clip module 300 in ligation clip applier 100, as ligation clip module 300 is pushed proximally in direction "A" within neck portion 120 of hollow shaft 122, a pin 127 disposed within hollow shaft 122 will engage a detent 301 disposed on an outer surface of ligation clip module 300. Detent 301 of ligation clip module 300 serves to prevent ligation clip module from being pushed further proximally within hollow shaft 122.

In this position, once loaded, a surgeon may partially squeeze trigger 114, which urges advancing shaft 132 distally and engages a proximal end of pusher 310. Bumps 302, disposed within ligation clip module 300, will abut a distal end 311 of pusher 310 and prevent pusher 310 from advancing further distally in direction "B" relative to ligation clip module 300. Likewise, retaining wings 312 will prevent pusher 310 from advancing further proximally in direction "A" relative to ligation clip module 300. Upon the partial actuation of trigger 114, the entire ligation clip module 300 will be advanced distally until stop 303 of ligation clip module 300 engages pawl 126a of latch 126 (FIG. 9) and prevents further distal movement of ligation clip module 300 within neck portion 120 of hollow shaft 122. Additionally, boss 304 is now in engagement with rim 122a of hollow shaft 122 FIG. 9A), which prevents accidental proximal or backward movement of ligation clip module 300 in direction "A" within neck portion 120 of hollow shaft 122. With ligation clip module 300 secured in place, a full actuation or squeeze of trigger 114 will cause distal end 311 of pusher 310 to overcome bumps 302 and engage and expel ligation clip 320 from neck portion 120 of hollow shaft 122.

Although specific embodiments of the present disclosure have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present disclosure which is defined in the following claims, the scope of which is to be accorded the broadest interpretation so as to encompass such modifications and equivalent structures.

What is claimed is:

1. A ligation clip module, comprising:
a module housing compressible from an uncompressed condition to a compressed condition, the module housing including:
a proximal portion and a distal portion;
a lumen extending therethrough;
an immobilizer extending into the lumen; and
an outer surface having a protrusion extending laterally outward therefrom;
a pusher slidably disposed in the lumen of the module housing, the pusher including a pusher body having an enlarged proximal portion and an enlarged distal portion; and
a ligation clip disposed in the proximal portion of the module housing at a location distal of the pusher;
wherein the module housing is compressed from the uncompressed condition to the compressed condition such that the protrusion of the module housing is advanceable into an open end of a distal end of a shaft of a ligation clip applier, and such that the proximal end of the module housing is selectively connected to the distal end of the shaft of the ligation clip applier,
wherein when the module housing is in the compressed condition, the immobilizer of the module housing is disposed between the enlarged proximal portion and the enlarged distal portion of the pusher body such that the pusher is prevented from axial movement within the module housing.

2. The ligation clip module according to claim 1, wherein, when the module housing is in the compressed condition and disposed in the distal end of the shaft of the ligation clip applier, the enlarged proximal portion of the pusher is engagable by an advancing mechanism of the ligation clip applier such that the enlarged proximal portion of the pusher engages the immobilizer of the module housing whereby the module is urged axially toward the distal end of the shaft of the ligation clip applier.

3. The ligation clip module according to claim 1, wherein when the protrusion of the module housing is urged distally past the distal end of the shaft of the ligation clip applier, the module housing is free to return to the uncompressed condition from the compressed condition.

4. The ligation clip module according to claim 1, wherein the ligation clip is a two-part ligation clip having a first part formed to be closed about a vessel and a second part moveable relative to the first part to cause the first part to close.

5. The ligation clip module according to claim 1, wherein the ligation clip is formed from a bioabsorbable material.

6. The ligation clip module according to claim 1, wherein the pusher includes retaining wings disposed on the pusher body for retaining the pusher in the module housing.

7. The ligation clip module according to claim 1, wherein the module housing includes a recess formed in the outer surface thereof for receiving a latch of the ligation clip applier, whereby the module housing is selectively fixedly secured to the distal end of the shaft of the ligation clip applier.

8. The ligation clip module according to claim 1, wherein the protrusion contacts an inner wall of the shaft when the module housing is in the compressed condition.

9. The ligation clip module according to claim 8, wherein the protrusion is free from contact with the inner wall of the shaft when the module housing is in the uncompressed condition.

10. The ligation clip module according to claim 1, wherein proximal movement of the module housing through the open end of the distal end of the shaft when the module housing is in the uncompressed condition causes the protrusion to contact a distal edge of the shaft thereby preventing additional proximal movement of the module housing relative to the shaft.

11. A ligation clip module for selective connection to a handle assembly of a ligation clip applier and actuatable by an advancing mechanism of the handle assembly, the ligation clip module comprising:
  a module housing compressible from an uncompressed condition to a compressed condition, the module housing including:
    an outer surface having a protrusion extending laterally outward therefrom;
    a proximal end being configured for selective connection to a distal end of a shaft of the ligation clip applier;
    a distal end; and
    a lumen extending therethrough and having an immobilizer extending thereinto;
  a pusher slidably disposed in the lumen of the module housing, the pusher including a pusher body having an enlarged proximal portion and an enlarged distal portion; and
  a ligation clip slidably disposed in the lumen of the module housing at a location distal of the pusher;
  wherein the module housing is compressed from the uncompressed condition to the compressed condition such that the protrusion of the module housing is advanceable into an open end of the distal end of the shaft of the ligation clip applier, and such that the proximal end of the module housing is selectively connected to the distal end of the shaft of the ligation clip applier, and wherein the module housing is maintained in the compressed condition when the protrusion of the module housing is within the shaft of the ligation clip applier; and
  wherein, when the module housing is in the compressed condition, the immobilizer of the module housing is disposed between the enlarged proximal portion and the enlarged distal portion of the pusher body such that the pusher is prevented from axial movement within the module housing.

12. The ligation clip module according to claim 11, wherein, when the module is in the compressed condition and disposed in the distal end of the shaft of the ligation clip applier, the enlarged proximal portion of the pusher is engagable by the advancing mechanism of the handle assembly of the ligation clip applier such that the enlarged proximal portion of the pusher engages the immobilizer of the module housing whereby the module is urged axially toward the distal end of the shaft of the ligation clip applier.

13. The ligation clip module according to claim 11, wherein when the protrusion of the module housing is urged distally past the distal end of the shaft of the ligation clip applier, the module housing is free to return to the uncompressed condition.

14. The ligation clip module according to claim 11, wherein the ligation clip is a two-part ligation clip having a first part formed to be closed about a vessel and a second part moveable relative to the first part to cause the first part to close.

15. The ligation clip module according to claim 11, wherein the ligation clip is formed from a bioabsorbable material.

16. The ligation clip module according to claim 11, wherein the pusher includes retaining wings disposed on the pusher body for retaining the pusher in the module housing.

17. The ligation clip module according to claim 11, wherein the module housing includes a recess formed in the outer surface thereof for receiving a latch of the ligation clip applier, whereby the module housing is selectively fixedly secured to the distal end of the shaft of the ligation clip applier.

18. The ligation clip module according to claim 11, wherein the protrusion contacts an inner wall of the shaft when the module housing is in the compressed condition.

19. The ligation clip module according to claim 18, wherein the protrusion is free from contact with the inner wall of the shaft when the module housing is in the uncompressed condition.

20. The ligation clip module according to claim 11, wherein proximal movement of the module housing through the open end of the distal end of the shaft when the module housing is in the uncompressed condition causes the protrusion to contact a distal edge of the shaft thereby preventing additional proximal movement of the module housing relative to the shaft.

* * * * *